United States Patent [19]
Boettner et al.

[11] 3,991,180
[45] Nov. 9, 1976

[54] STABILIZATION OF INTERNALLY ADMINISTERED PANCREATIC LIPASE

[75] Inventors: Fred E. Boettner, Huntingdon Valley; Clifford E. Neubeck, Hatboro, both of Pa.

[73] Assignee: Rohm and Haas Company, Philadelphia, Pa.

[22] Filed: Oct. 7, 1974

[21] Appl. No.: 512,743

Related U.S. Application Data

[63] Continuation-in-part of Ser. No. 232,291, March 6, 1972, abandoned.

[52] U.S. Cl. .................................. 424/94; 424/14
[51] Int. Cl.² ..................................... A61K 37/48
[58] Field of Search ............................ 424/94

[56] References Cited
UNITED STATES PATENTS

| | | | |
|---|---|---|---|
| 3,081,225 | 3/1963 | Farnham et al. | 424/94 |
| 3,256,150 | 6/1966 | Nelson et al. | 424/94 |

FOREIGN PATENTS OR APPLICATIONS

| | | | |
|---|---|---|---|
| 1,235,540 | 6/1971. | United Kingdom | 424/94 |

OTHER PUBLICATIONS

Downey et al., Chem. Abstr., vol. 72 (1970) p. 118050f.
Shani et al., Arch. Biochem. & Biophysics, vol. III (1965) pp. 257–263.

*Primary Examiner*—Sam Rosen
*Attorney, Agent, or Firm*—Terence P. Strobaugh; George W. F. Simmons; Carl A. Castellan

[57] ABSTRACT

A method for treating exocrine pancreatic insufficiency is disclosed. The method comprises the administration of a stable solid medicinal preparation containing finely particulated lipase intimately admixed with Hammarsten's casein and a tabletting lubricant, whereby a hydraulic pressure of about 2000 to about 5000 psi is employed.

4 Claims, No Drawings

STABILIZATION OF INTERNALLY ADMINISTERED PANCREATIC LIPASE

CROSS-REFERENCE TO RELATED APPLICATION

This application is a continuation-in-part of U.S. Ser. No. 232,291 filed Mar. 6, 1972 now abandoned.

This invention relates to a method of treating exocrine pancreatic insufficiency by the administration of exogenous lipase and to a medicinal preparation of lipase which is substantially resistant to gastric disintegration.

It is known that by adding a protein or a partially hydrolyzed protein, such as gelatin or partially hydrolyzed gelatin, respectively, to aqueous solutions of proteolytic enzymes, it is possible to effect some stabilization of the enzymic activity; however, at best, the enzymes in such stabilized solutions retain their activities for limited periods. The stability of lipase in a harsh acid medium, like gastric juice, is almost nonexistent.

BACKGROUND OF THE INVENTION

Prior art, for example, U.S. Pat. Nos. 3,081,225 and 3,256,150 are concerned with methods of orally administering to the afflicted, medicaments which are susceptible to attack by gastric acids. In these references, considerable stress is laid on the teaching that the combination of the enzyme, pregastric esterase and non-fat dry milk powder should be finally ground. It is clearly taught for administration as a powder, or as a powder to be encapsulated.

There is no suggestion in the prior art of a lipase enclosed in a selected matrix which will disintegrate in the intestinal portion of a mammalian G. I. tract. It is doubtful that dry fat milk solids with their high lactose content would offer protection to a drug which was sensitive to attack by gastric juices since lactose is highly soluble in water and acidic solutions.

U.S. Pat. No. 3,065,142 describes a gastric resistant pancreatin, a derivative of mammalian pancreas tissue containing a medicinal preparation, exemplified by a mixture of enzymes. However, this patent has a central teaching of treating the resulting mixture of medicinal agent and gastric resistant material with heat to liquify the gastric resistant material. The ultimate form of the preparation is granules, rather than tablets, substantially resistant to gastric disintegration. The present invention does not rely on a means which protects the sensitive medicinal agent by requiring utilization of heat to achieve the necessary intermixing.

Another reference of interest is the Italian journal *Il Farmaco*, Vol. 22, p. 585, 1967 (Oct.). Therein the authors suggest the use of whole powdered skim milk to protect the activity of pancreatic enzymes. However, this material is also certainly subject to attack because of its high percentage of water-soluble lactose.

It is, therefore, a principal object of the invention to stabilize internally administered pancreatic lipase in the presence of gastric juice.

It is another object to increase the amount of active pancreatic lipase passing intact through the mammalian stomach to the intestinal tract.

It is another object to reduce the amount of exogenously provided pancreatin required to achieve an acceptable degree of relief of exocrine pancreatic insufficiency.

It is another object to provide formulated pancreatic lipase, in a dosage unit form, aiding in increasing protein and fat absorption in the mammalian gastrointestinal tract.

Lipase of pancreatic origin is generally recognized as unstable in an acid environment. The present invention provides means for substantially preventing the denaturation of this pancreatic enzyme by gastric acid, while at the same time, retaining its enzymatic activity in the intestinal environment.

According to the present invention, there is provided a method of treating exocrine pancreatic insufficiency in mammals by treating said mammals with an effective amount of a stable, solid medicinal preparation containing pancreatic lipase and Hammarsten's casein which preparation is substantially resistant to gastric disintegration. The medicament is prepared by a method which comprises:

a. intimately admixing from about 10 to about 34% lipase solid (% by weight) of finely particulated active lipase having a maximum particle size of 450 microns and preferably a maximum particle size of 150 microns and from about 66 to about 90% by weight of finely particulated Hammarsten's casein having a maximum particle size of 450 microns and preferably a maximum particle size of 150 microns;

b. a sufficient amount of a conventional water insoluble or only slightly water insoluble pharmaceutically acceptable tabletting lubricant such as stearic acid, magnesium stearate, calcium stearate and the like to facilitate tabletting of the resulting powdered medicament;

c. subjecting said medicament to tabletting in a tabletting means at a hydraulic pressure of from about 2000 to 5000 psi for a period of time sufficient to insure structural integrity on release from the press of the resulting tablet.

The results from the foregoing provide an acid-stable lipase containing medicament in tablet form having:

a. a major portion of the active lipase in finely particulated form;

b. the acid insoluble orally disintegratable Hammarsten's casein, in particulate form; and c. a pharmaceutically acceptable tabletting lubricant in an amount sufficient to insure structural integrity of the resulting tablet during manufacture.

The acid-stable compositions of the present invention are prepared to contain from about 100 to 500 mg. of the active lipase N. F. in dosage unit form. Preferably about 200 to 250 mg. of the lipase N. F. is provided in each of the preferred tablets. It is axiomatic in this area of therapy that the exact dosage regimen will depend to a major extent on the strength of the pancreatin used. The daily dosage regimen is 400 to 2400 mg. in divided dosage, three times daily after meals.

Pancreatin is a substance containing enzymes, principally amylase, protease, and lipase, obtained from the pancreas of the hog *Sus scrofa* Linne var. *domesticus* Gray (Fam. Suidae); or of the ox, *Bos taurus* Linne (Fam. Bovidae).

Pancreatin N.F. converts not less than 25 times its weight of N.F. Potato Starch Reference Standard into soluble carbohydrates and not less than 25 times its weight of casein into proteoses. Pancreatin of a higher digestive power may be labeled as a whole number multiple of the two minimum activities or may be diluted by admixture with lactose or with sucrose containing not more than 3.25% of starch or with pancreatin of lower digestive power.

Pancreatin 4XNF has four times the activity of Pancreatin NF. Hammarsten's casein is casein purified by the Hammarsten method [Hammarsten, Textbook of Physiological Chemistry, 7th ed., New York, 1911, p. 619] and can be purchased from Nutrional Biochemicals Corp., Cleveland, Ohio.

The General Services Administration (GSA) method of determining pancreatic activity is based on the ability of an enzyme preparation to hydrolyze fatty acids from an emulsion of olive oil. The olive oil method is "Method B" of the General Services Administration [Interim Federal Specification P. C-0044b (GSA-FSS), Feb. 20, 1963]. The GSA activity of an enzyme is defined as the ml. of N. acid produced by 1 gram of enzyme from 1.25 ml. (1.14 g.) of olive oil at the assay pH in 2 hours at 37° C. when calculated at the 5.25% level of substrate hydrolysis. Since complete alkaline saponification of 1.14 g. olive oil liberates 76.03 ml. of 0.05 N. acid, then 5.25% hydrolysis is equal to 4.00 ml. of 0.05 N. acid.

$$GSA/gram = \frac{[4.0 \text{ ml.} \times 0.05 \text{ N. NaOH}] \times 1000}{\text{mg. of enzyme required to produce } 4.00 \text{ ml. } 0.05 \text{ acid}}$$

EXAMPLE I

Wilson 3000 Lipase (Pancreatin 4X or 5X N. F., containing 250 GSA Units/gram) is ground in a micromill at 0° C., for 3 minutes, and then screened through a 100-mesh screen (glass beads were used during the screening operation). One volume of screened Wilson 3000 Lipase (3.8335 g.) is mixed with 3 volumes of Hammarsten's casein (17.2397 g.) which was also screened (100 mesh) and mixed in the micromill at 0° C. for 30 seconds. This mixture, excluding lubricant, contains 18.19% Wilson Lipase on a weight basis and 25% Wilson Lipase on a volume basis. Fifteen samples (ca 0.4 g.) of this mixture are weighed and compressed into tablets using a Carver press at 1000 psi hydraulic pressure, using ½ inch diameter flat-faced tablet die. (These tablets had an average weight of 0.4034 g.; range 0.3979–0.4080 g.)

In preparing these tablets, the mixture is placed in the tablet die, compressed as rapidly as possible (3 to 4 seconds) to the desired pressure and the pressure immediately released.

Table I (infra) shows the determination of lipase activity of pure lipase and mixtures of lipase and Hammarsten's casein tabletted at 1000 psi. Three tablets prepared as above but without any lubricant are placed in plastic screen baskets, which are disposed in stirred simulated gastric juice (pH 1.2) at 37° C for various times. After the times noted (see Table I), the tablets were removed, dried overnight in a vacuum desiccator over $P_2O_5$ at room temperature, reweighed to determine weight loss, ground to a fine powder in a mortar and pestle and the Lipase activity determined.

TABLE I

| | TABLETS PREPARED AT 1000 PSI | | | |
|---|---|---|---|---|
| Sample No. | Description | % Wt. Loss After Exposure | Lipase Activity GSA/g | % Original Tablet Activity |
| — | Wilson 3000 Lipase | — | 122.0 | — |
| Control | Lipase-casein before tabletting | — | 28.6* | — |
| Tablet | Tabletted mixture of Lipase casein | — | 28.6 | 100 |
| A | After 30 min. in gastric juice | 8.46 | 18.2 | 63.6 |
| B | After 60 min. in gastric juice | 10.45 | 11.4 | 40.0 |
| C | After 90 min. in gastric juice | 9.10 | 6.05 | 21.1 |
| D | After 120 min. in gastric juice | 9.82 | 3.70 | 12.9 |

*The theoretical Lipase activity based on wt. % Lipase should be 22.2 GSA/g

EXAMPLE II

The experiment was repeated using the same casein-Lipase mixture, with the tablets prepared at 1500 psi hydraulic pressure (18 tablets; avg. wt. = 0.4073 g. range = 0.4038 – 0.4096 g.). The results from this experiment are shown in Table II.

Three of the casein-Lipase tablets prepared at 1000 psi were found to disintegrate within 15–20 minutes in stirred simulated intestinal fluid (pH 7.4) at 37° C. Two out of three of the tablets prepared at 1500 psi had turned to a swollen soft paste in 20 minutes under these conditions and had dispersed completely in 60 minutes.

A third tablet (2000 psi) was badly swollen and cracked in 20 minutes and was a soft mass in 60 minutes.

The results of these experiments in gastric juice, when plotted on semi-log paper, show a first order loss of Lipase activity with time. A plot will show a half-time loss of about 45 minutes for the 1000 psi tablets and about 75 minutes for the 1500 psi tablets.

The data in Tables I and II show the limited degree of stabilization of Lipase by casein.

TABLE II

| | TABLETS PREPARED AT 1500 PSI | | | |
|---|---|---|---|---|
| Sample | Description | % Wt. Loss After Exposure | Lipase Activity GSA/g | % Original Tablet Activity |
| Wilson 3000 Lipase Control | — Untabletted | — | 118.0 | — |
| | Lipase-casein before tabletting | — | 29.4* | — |
| Tablet | Tabletted mixture of lipase-casein | — | 28.6 | 100.0 |
| A | After 30 min. in gastric juice | 5.86 | 22.2 | 77.6 |
| B | After 60 min. in gastric juice | 7.34 | 16.7 | 58.4 |
| C | After 90 min, in gastric juice | 7.84 | 12.5 | 43.7 |
| D | After 120 min. in gastric | | | |

3,991,180

TABLE II-continued

| | TABLETS PREPARED AT 1500 PSI | | | |
|---|---|---|---|---|
| Sample | Description | % Wt. Loss After Exposure | Lipase Activity GSA/g | % Original Tablet Activity |
| | juice | 10.37 | 9.6 | 33.6 |

*The theoretical Lipase activity based on the wt. % Lipase should be 21.46 GSA/g.

EXAMPLE III

Additional sample tablets, formulated from Wilson 300 Lipase and Hammarsten's casein are prepared as before employing 3000 psi for tabletting. Each of the candidate formulations was evaluated at three levels. The quantity of material required to produce 4 ml. titration in the test method was determined. With the Wilson 3000 being run similarly, an average value of 250 GSA units (at pH 6) was obtained in tests run on 4 days.

The tablets prepared at 3000 psi showed 90% retention of Lipase activity after 120 minutes in gastric juice.

TABLE III

| | | Tablets Prepared at 3000 psi | | |
|---|---|---|---|---|
| Sample | Composition | Treatment | Expected Activity Based on Lipase Content GSA/g. | Activity Found GSA/g. | % Activity Retained |
| — | Wilson 3000 Lipase | None | — | 250 | — |
| A | 18.45% Lipase + casein | None | 46 | 71 | — |
| B | Tabletted A mixture | 210 min. in gastric juice | 46 | 64 | 90.1 |
| C | 33.4% Lipase + casein | None | 84 | 146 | — |
| D | Tabletted C mixture | 120 min. in gastric juice | 84 | 133 | 91.1 |

The data given in Tables I through III show the profound effect of the tabletting pressure on the stabilizing activity of casein on Lipase in gastric juice. Table IV is a summary of the data given in Tables I through III.

TABLE IV (Summary)
Effect of Tabletting Pressure on Stability in Gastric Juice

| Tablets Prepared At | Composition | % of Original Activity after 2 hours exposure to gastric juice at 37° C. |
|---|---|---|
| 1000 psi | 18.19% Lipase* + Casein | 12.9 |
| 1500 psi | 18.19% Lipase + Casein | 33.6 |
| 3000 psi | 18.45% Lipase + Casein | 90.1 |
| 3000 psi | 33.4% Lipase + Casein | 91.1 |

*Wilson 3000 Lipase

The data given in Tables I through III indicate that casein imparts an added stability to the Lipase, in addition to the protective effect exhibited by the tabletted mixture in the gastric exposure tests. It is readily apparent that each of the untabletted compositions prepared showed a greater activity in the GSA method than expected on the basis of the activity of the Wilson 3000 Lipase. The compositions showed 28%, 41%, 54% and 86% more activity than expected for the materials listed in Tables I, II and III (mixtures A and C). This increase in activity of Pancreatin due to casein may be a protective system.

At the pH (6.0) used in the GSA method, there may be a significant denaturation of the Lipase at the dilution used. Table V demonstrates that Pancreatin (Wilson 3000 Lipase) exhibits a marked loss of activity when allowed to sit at room temperature in aqueous solution for relatively short periods of time.

TABLE V

| Exposure Conditions | | GSA Activity |
|---|---|---|
| Wilson 3000 | held ½ hour at 0.1% before test* | 250 |
| | held ½ hr. at 0.016% before test** | 276 |
| | held ½ hr. at 0.1% then 3½ hr. at .016% | 141 |
| | held 4 hrs. at 0.1% | 96 |
| | held 4 hrs. at 0.016% | 140 |

*Normal solution concentration and incubation period used for solutions of enzyme in the GSA method. The enzyme concentration is 25 × the level finally achieved in the method.
**Enzyme solution level equivalent to 4 × the final level required for Wilson 3000 Lipase to give the specified hydrolysis in the GSA method.

The data given in examples I through III show the in vitro effect of casein on lipase stability. The following examples show the in vivo activity of the inventive mixtures in mammals.

EXAMPLE IV

Two different nutrient absorption experiments were performed in the pancreatic duct ligated (PDL) swine. Experiment IV was conducted using 6 female PDL Yorkshire swine, weighing 9–11 kg. The casein-pancreatin tablets were prepared as described earlier and contained 234 mg. Viokase (Pancreatin 4X N.F., Viobin Corp., essentially equivalent to Wilson 3000 Lipase), 468 mg. casein, and 3.5 mg. calcium stearate. The control tablets contained 350 mg. Viokase and 1.8 mg. calcium stearate.

The absorption studies began 1 week following duct ligation. During these studies the animals were kept in metabolism cages in which coprophagy was prevented. The animals were fed approximately 300 g. Purina dog meal, twice daily. $Cr_2O_3$ was added at 0.5% of the diet. This diet was selected because it contained approximately 10% animal fat, which is not readily absorbed even by normal swine. During the first week of study (pre-treatment period), the swine were fed the dog meal without pancreatin tablets. On the 6th and 7th days of the pre-treatment period, total fecal collections were made and were analyzed for nitrogen (protein), fat, and $Cr_2O_3$. The ratios of nutrient to $Cr_2O_3$ in feed and feces were used to calculate the percentage of ingested nutrient absorbed.

After the pre-treatment period, the swine were continued on the same feeding schedule, except that three pigs received 5 control tablets (Viokase), and the other three received 5 casein-Viokase tablets before each meal. This treatment period lasted 9 days, and 48-hour fecal collections were made on days 4 and 5, 6 and 7, 8 and 9. A post-treatment week followed during which time no tablets were administered.

This Example IV originally had six pigs, but the data from one animal was excluded when it was found that this pig was not totally exocrine pancreatic deficient. Both pretreatment/post-treatment absorption and the pancreatic function test indicated normal pancreatic secretion. The nutrient absorption data are presented in Table VI.

In terms of increasing nutrient absorption, the tablets containing casein plus Viokase, were as effective as those containing Viokase alone, despite the fact that the former contain only ⅔ as much pancreatin as the latter.

It is also noteworthy, that the animal in Example IV, which was eliminated because of retaining normal pancreatic function, adsorbed 75% and 76% of the protein and fat ingested during the post-treatment week. In the treated PDL swine, fat absorption was over 70% at times, while protein uptake was never more than 66%.

is illustrative of the protective action of casein on pancreatin, however, it is not the preferred method of this invention. The preparation of cored tablets is much more complicated and expensive than from a simple mixture of casein and pancreatin.

EXAMPLE V

The next experiment was performed using 9 PDL'd West African guinea hogs weighing 8–10 kg. In this study, 250 g. of a commercial swine diet containing 20% corn oil (w/w) was fed twice daily. $Cr_2O_3$ was also included in this diet at 0.5%. The study was conducted similarly to Experiment IV with a pretreatment week, two treatment weeks, and one post-treatment week.

During the treatment weeks, the swine were administered 2 tablets of either Wilson Lipase 3000 (pancreatin 400 mg/tablet) or Wilson Lipase 3000 coated with casein. These tablets were prepared in the manner conventional for preparing cored tablets. The latter each contained 200 mg. of the pancreatin and 200 mg. of casein. Fecal collections were made on the 6th and 7th days of each study week, and were analyzed for $Cr_2O_3$ and fat, to calculate the percentage nutrient absorbed.

The data obtained from this experiment are shown in Table VII. Here again, there were no significant differences between the responses obtained with the 400 mg. pancreatin tablets, and the tablets containing 200 mg. casein with a 200 mg. pancreatin core. Body weights in both groups remained stable during the study.

Both studies were preliminary in nature, being conducted to determine whether or not casein could replace a portion of the pancreatin. The results suggest that at the doses used casein may be substituted for up to ½ of the pancreatin and still obtain the desired degree of relief of the symptoms of pancreatic insuffi-

TABLE VI

Fat Absorption by PDL Yorkshire swine treated with Viokase or Viokase plus Casein

| Treatment[a] | Animal No. | Pre-treatment week | Coefficient of Fat Absorption[b] during | | | Post-treatment week |
|---|---|---|---|---|---|---|
| | | | Treatment days | | | |
| | | | 4 and 5 | 6 and 7 | 8 and 9 | |
| Casein + | 198 | 26.5 | 71.5 | 63.8 | 70.7 | 37.5 |
| Viokase | 217 | 6.3 | 70.4 | 76.4 | 18.5 | C |
| | 211 | 31.7 | 69.7 | 72.0 | 39.4 | 39.3 |
| Viokase | 214 | −6.6 | 62.5 | 53.1 | 56.3 | 8.8 |
| | 216 | −8.5 | 70.7 | 63.1 | 65.3 | 21.6 |

[a]Tablets contained either 234 mg. Viokase plus 468 mg. Casein or 350 mg. Viokase. During the treatment periods the pigs received 5 tablets just prior to their 2 daily feedings of 300 g. Purina dog meal.
[b]Percentage of ingested fat not excreted.
[c]Representative fecal samples not obtainable because of severe diarrhea, poor sample obtained on days 8 and 9.

In the examples I through IV the tablets used were prepared from mixtures of pancreatin and casein. In examples V and VI "cored" tablets of pancreatin coated with casein were used. This use of cored tablets ciency. This makes it possible to obtain the maximum activity from the Pancreatin dosed at a lower cost per unit dose.

TABLE VII

Fat absorption by PDL swine after treatment with Pancreatin or Casein-Coated Pancreatin tablets.

| Treatment[a] | No. per group | Fat Absorption during[b] | | | Post-treatment |
|---|---|---|---|---|---|
| | | Pre-treatment | Treatment week | | |
| | | | 1 | 2 | |
| Casein-coated Pancreatin Pancreatin | 4 | 3.9±19.4 | 59.4±4.9 | 65.2±2.4 | 20.0±8.5 |

TABLE VII-continued

Fat absorption by PDL swine after treatment with Pancreatin or Casein-Coated Pancreatin tablets.

| Treatment[a] | No. per group | Fat Absorption during[b] | | | Post-treatment |
|---|---|---|---|---|---|
| | | Pre-treatment | Treatment week 1 | 2 | |
| Alone | 5 | 4.0±6.0 | 62.5±7.4 | 61.8±5.6 | 24.4±9.2 |

[a]Tablets containing 200 mg. casein with 200 mg. pancreatin (Wilson Lipase 3000) core compared to tablets containing 400 mg. pancreatin alone. During treatment weeks, 2 tablets were administered just prior to each twice daily feeding of 250 g swine diet containing 20% corn oil.
[b]Percentage of ingested fat not excreted. Mean ± 1 SEM.

EXAMPLE VI

A third study was performed to determine the stability of the casein-coated tablets in the stomach of the PDL swine. Each of three PDL West African Guinea swine were fasted for 24 hours, and then dosed with 5 of the casein-coated pancreatin tablets, 5 of the 400 mg. Wilson Lipase 3000 tablets, and 5 [Cotazym] capsules (275 mg. pancreatin plus 25 mg. $CaCO_3$ per capsule). Two pigs were sacrificed after 15 minutes, and the third after one hour, for examination of stomach contents.

In this in vivo stability study, it was found that at 15 minutes after dosing, the Cotazym capsules were completely disintegrated, and the 400 mg. pancreatin tablets were reduced in size. The casein-coated pancreatin tablets were not visibly changed at 15 minutes, and only slightly swollen after 60 minutes. By 60 minutes, the uncoated pancreatin tablets were markedly reduced in size.

This observation serves only to point out the stability of casein-coated pancreatin in gastric contents and explains some unsuccessful attempts to detect lipase and protease activity in the jejunum of PDL swine dosed with these tablets. At some time, however, the casein-coated tablets or their contents must leave the stomach since they do promote digestion in exocrine pancreatic deficient swine.

The invention disclosed herein can be applied to any drug that needs protection in the presence of gastric juice (enterically coated drugs).

What is claimed is:

1. An acid stable, lipase containing medicament in tablet form, for treating pancreatic insufficiency comprising:
   a. from about 10 to about 34% by weight of an active lipase having a maximum particle size of 450 microns;
   b. from about 66 to about 90% by weight of Hammarsten's casein having a maximum particle size of 450 microns and
   c. a sufficient amount of a pharmaceutically acceptable tabletting lubricant said medicament being tabletted in a tabletting means at a hydraulic pressure of from about 2,000 to 5,000 psi to insure structural integrity of the tablet.

2. An acid stable lipase containing medicament in tablet form for treating pancreatic insufficiency which comprises:
   a. from about 10 to about 34% by weight of an active lipase having a maximum particle size of 150 microns;
   b. from about 66 to about 90% by weight of Hammarsten's casein having a maximum particle size of 150 microns and
   c. a sufficient amount of a pharmaceutically acceptable tabletting lubricant said medicament being tabletted in a tabletting means at a hydraulic pressure of from about 2,000 to 5,000 psi to insure structural integrity of the tablet.

3. A method of treating exocrine pancreatic insufficiency in mammals which comprises orally administering an effective amount of the medicament of claim 1.

4. A method of treating exocrine pancreatic insufficiency in mammals which comprises orally administering an effective amount of the medicament of claim 2.

* * * * *